US008540738B2

(12) United States Patent  (10) Patent No.: US 8,540,738 B2
Cavanaugh et al.  (45) Date of Patent: Sep. 24, 2013

(54) METHOD AND APPARATUS FOR DELIVERY OF A LIGATING SUTURE

(75) Inventors: Brian J. Cavanaugh, Hingham, MA (US); James J. A. Cavanaugh, Osterville, MA (US)

(73) Assignee: Cavanaugh Medical Devices, LLC, Hyannis, MA (US)

( * ) Notice: Subject to any disclaimer, the term of this patent is extended or adjusted under 35 U.S.C. 154(b) by 0 days.

(21) Appl. No.: 13/471,141

(22) Filed: May 14, 2012

(65) Prior Publication Data

US 2012/0226293 A1    Sep. 6, 2012

Related U.S. Application Data

(63) Continuation of application No. 12/187,486, filed on Aug. 7, 2008, now abandoned.

(60) Provisional application No. 60/963,958, filed on Aug. 8, 2007.

(51) Int. Cl.
*A61B 17/04* (2006.01)

(52) U.S. Cl.
USPC .............................. 606/148; 606/139; 606/144

(58) Field of Classification Search
None
See application file for complete search history.

(56) References Cited

U.S. PATENT DOCUMENTS

| 4,046,149 A | 9/1977 | Komiya |
| 4,069,825 A | 1/1978 | Akiyama |
| 4,202,338 A | 5/1980 | Bitrolf |
| 4,643,187 A | 2/1987 | Okada |
| 5,026,371 A | 6/1991 | Rydell et al. |
| 5,035,688 A | 7/1991 | Inui |
| 5,066,295 A | 11/1991 | Kozak et al. |
| 5,122,147 A | 6/1992 | Sewell, Jr. |
| 5,123,913 A | 6/1992 | Wilk et al. |
| 5,158,561 A | 10/1992 | Rydell et al. |
| 5,171,314 A | 12/1992 | Dulebohn |
| 5,190,542 A | 3/1993 | Nakao et al. |
| 5,207,686 A | 5/1993 | Dolgin |
| 5,244,801 A | 9/1993 | Tobi |
| 5,281,238 A | 1/1994 | Chin et al. |
| 5,336,227 A | 8/1994 | Nakao et al. |

(Continued)

OTHER PUBLICATIONS

Preliminary Report on Patentability mailed Feb. 18, 2010 PCT Application No. PCT/US2008/072443.

(Continued)

*Primary Examiner* — Corrine M McDermott
*Assistant Examiner* — Todd J Scherbel
(74) *Attorney, Agent, or Firm* — Wolf, Greenfield & Sacks, P.C.

(57) ABSTRACT

An apparatus for ligating a medical protrusion comprises a ligating suture having a proximal end and a distal end configured to circumscribe the medical protrusion, and a one-way lock positioned there between. The apparatus further comprises an endoscope, a cutter blade configured to cut the suture, and a device for ligating a medical protrusion. The device comprises a tubular body having a proximal end and a distal end, a handle positioned at the proximal end, an endoscope controller operably connectable to the endoscope, a cutting controller operably connectable to the cutter blade, a suture controller configured to be operatively coupled with the suture, a curved bridge positioned at the distal end, the bridge having a proximal end and a distal end, and an armature, having a proximal end and a distal end, configured to releaseably retain at least a portion of the suture.

19 Claims, 11 Drawing Sheets

(56) References Cited

U.S. PATENT DOCUMENTS

| | | |
|---|---|---|
| 5,376,094 A | 12/1994 | Kline |
| 5,417,697 A | 5/1995 | Wilk et al. |
| 5,423,830 A | 6/1995 | Schneebaum et al. |
| D362,504 S | 9/1995 | Younker et al. |
| 5,458,111 A | 10/1995 | Coin |
| 5,462,553 A | 10/1995 | Dolgin |
| 5,480,407 A | 1/1996 | Wan et al. |
| 5,486,182 A | 1/1996 | Nakao et al. |
| 5,520,691 A | 5/1996 | Branch |
| 5,549,619 A * | 8/1996 | Peters et al. ............ 606/151 |
| 5,575,694 A | 11/1996 | Hawkins et al. |
| 5,595,565 A | 1/1997 | Treat et al. |
| 5,599,299 A | 2/1997 | Weaver et al. |
| 5,651,788 A | 7/1997 | Fleischer et al. |
| 5,741,271 A | 4/1998 | Nakao et al. |
| 5,746,694 A | 5/1998 | Wilk et al. |
| 5,746,747 A | 5/1998 | McKeating |
| 5,759,187 A | 6/1998 | Nakao et al. |
| 5,763,435 A | 6/1998 | Setchell |
| 5,766,217 A | 6/1998 | Chisty |
| 5,788,681 A | 8/1998 | Weaver et al. |
| 5,814,052 A | 9/1998 | Nakao et al. |
| 5,843,028 A | 12/1998 | Weaver et al. |
| 5,846,248 A | 12/1998 | Chu et al. |
| 5,906,620 A | 5/1999 | Nakao et al. |
| 5,906,621 A | 5/1999 | Secrest et al. |
| 5,938,586 A | 8/1999 | Wilk et al. |
| 5,947,979 A | 9/1999 | Ouchi et al. |
| 5,961,526 A | 10/1999 | Chu et al. |
| 5,968,056 A | 10/1999 | Chu et al. |
| 5,984,933 A | 11/1999 | Yoon |
| 5,989,264 A | 11/1999 | Wright |
| 5,997,547 A | 12/1999 | Nakao et al. |
| 6,010,512 A | 1/2000 | Chu et al. |
| 6,015,415 A | 1/2000 | Avellanet |
| 6,050,995 A | 4/2000 | Durgin |
| 6,071,233 A | 6/2000 | Ishikawa et al. |
| 6,083,202 A | 7/2000 | Smith |
| 6,090,131 A | 7/2000 | Daley |
| 6,171,315 B1 | 1/2001 | Chu et al. |
| 6,190,384 B1 | 2/2001 | Ouchi |
| 6,193,717 B1 | 2/2001 | Ouchi |
| 6,210,416 B1 | 4/2001 | Chu et al. |
| 6,231,888 B1 | 5/2001 | Lerner et al. |
| 6,235,026 B1 | 5/2001 | Smith |
| 6,251,884 B1 | 6/2001 | Setchell |
| 6,258,064 B1 | 7/2001 | Smith et al. |
| 6,306,819 B1 | 10/2001 | Rupnick et al. |
| 6,312,599 B1 | 11/2001 | Reid |
| 6,315,782 B1 | 11/2001 | Chu et al. |
| 6,346,106 B1 | 2/2002 | Jako |
| 6,375,650 B1 | 4/2002 | Ouchi |
| 6,375,661 B2 | 4/2002 | Chu et al. |
| 6,383,194 B1 | 5/2002 | Pothula |
| 6,428,548 B1 | 8/2002 | Durgin et al. |
| 6,471,987 B1 | 10/2002 | McBride-Sakal et al. |
| 6,517,538 B1 | 2/2003 | Jacob et al. |
| 6,572,578 B1 | 6/2003 | Blanchard |
| 6,616,654 B2 | 9/2003 | Mollenauer |
| 6,616,659 B1 | 9/2003 | de la Torre et al. |
| 6,638,286 B1 | 10/2003 | Burbank et al. |
| 6,692,445 B2 | 2/2004 | Roberts et al. |
| 6,726,896 B2 | 4/2004 | Tait |
| 6,730,097 B2 | 5/2004 | Dennis |
| 6,736,812 B2 | 5/2004 | Kear |
| 6,743,206 B1 | 6/2004 | Smith et al. |
| 6,770,066 B1 | 8/2004 | Weaver et al. |
| 6,773,432 B1 | 8/2004 | Clayman et al. |
| 6,814,739 B2 | 11/2004 | Secrest et al. |
| 6,849,078 B2 | 2/2005 | Durgin et al. |
| 6,908,427 B2 | 6/2005 | Fleener et al. |
| 6,911,032 B2 | 6/2005 | Jugenheimer et al. |
| 6,947,784 B2 | 9/2005 | Zalis |
| 7,037,307 B2 | 5/2006 | Dennis |
| 7,044,947 B2 | 5/2006 | de la Torre et al. |
| 7,052,495 B2 | 5/2006 | Smith |
| 7,063,661 B2 | 6/2006 | Okada |
| 7,063,671 B2 | 6/2006 | Couvillon, Jr. |
| 7,101,378 B2 | 9/2006 | Salameh et al. |
| 7,115,091 B2 | 10/2006 | Root et al. |
| 7,189,223 B2 | 3/2007 | Kear |
| 7,193,519 B2 | 3/2007 | Root et al. |
| 2003/0023237 A1 | 1/2003 | Mollenauer |
| 2003/0109874 A1 | 6/2003 | Dennis |
| 2003/0236535 A1 | 12/2003 | Onuki et al. |
| 2004/0044335 A1 | 3/2004 | de la Torre et al. |
| 2004/0127915 A1 | 7/2004 | Fleenor et al. |
| 2005/0043743 A1 | 2/2005 | Dennis |
| 2005/0043744 A1 | 2/2005 | Tu |
| 2005/0131403 A1 | 6/2005 | Chang |
| 2006/0025780 A1 | 2/2006 | James |
| 2006/0253128 A1 | 11/2006 | Sekine et al. |
| 2007/0198035 A1 * | 8/2007 | Threlkeld ............ 606/148 |
| 2008/0243183 A1 | 10/2008 | Miller et al. |
| 2008/0294175 A1 | 11/2008 | Bardsley et al. |
| 2008/0312664 A1 * | 12/2008 | Bardsley et al. ............ 606/142 |
| 2010/0069925 A1 * | 3/2010 | Friedman et al. ............ 606/144 |

OTHER PUBLICATIONS

International Search Report and Written Opinion mailed Feb. 26, 2009 for PCT Application No. PCT/US2008/072443.

* cited by examiner

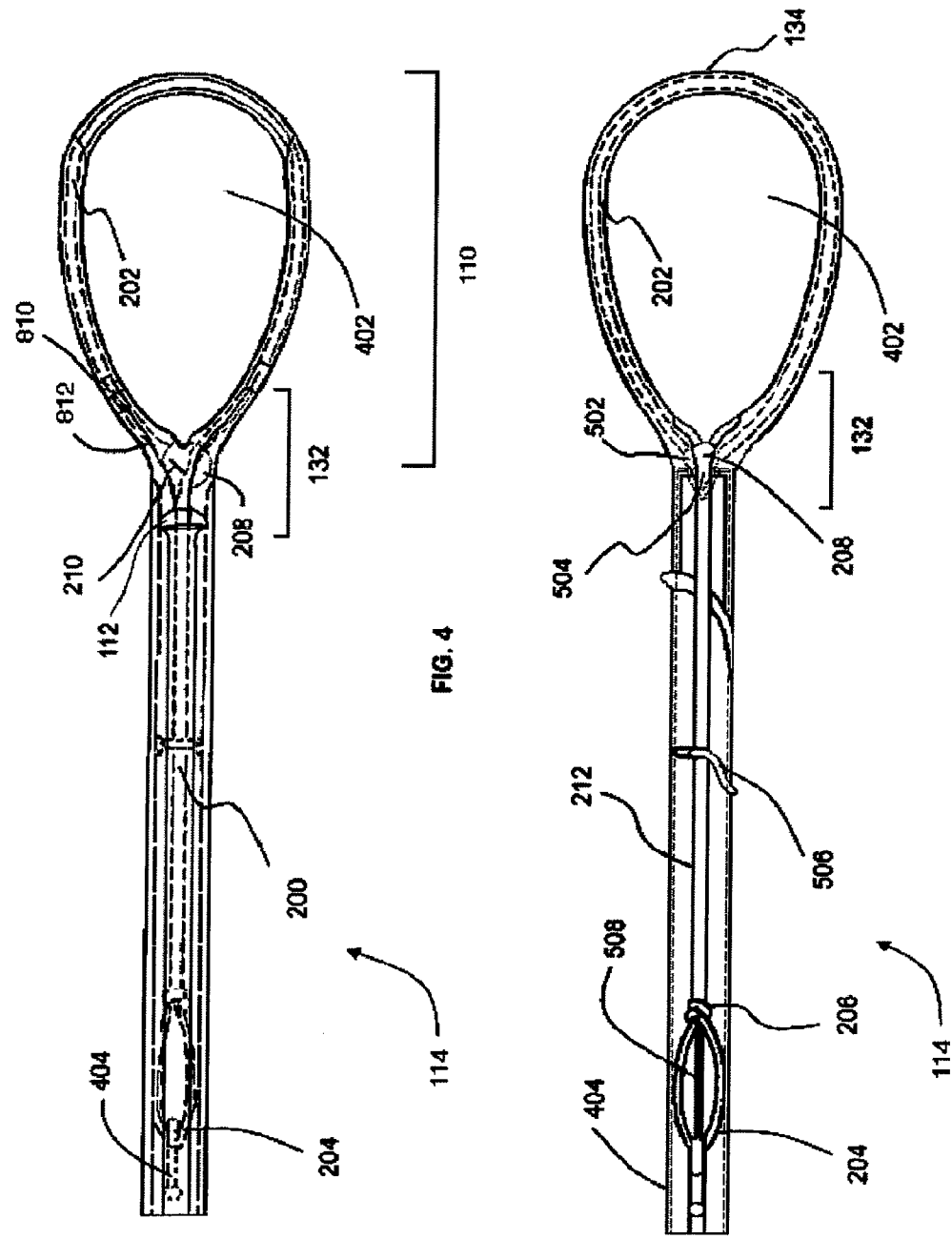

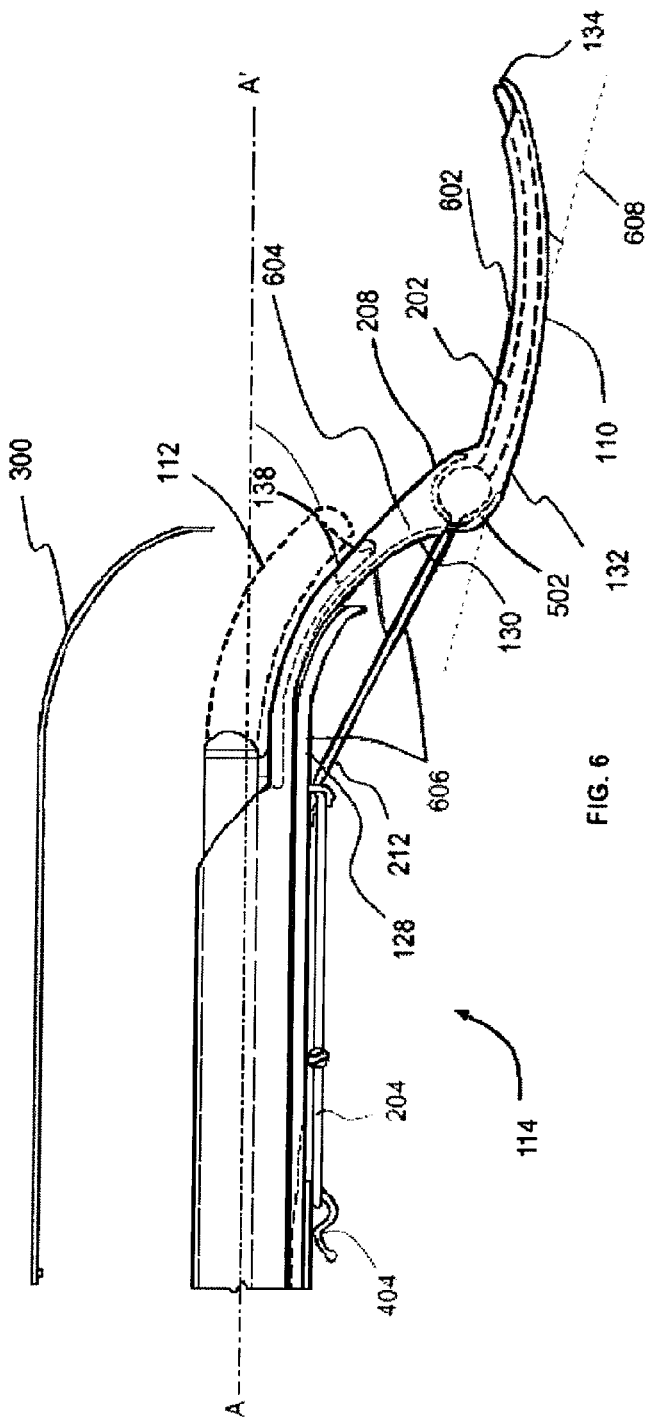
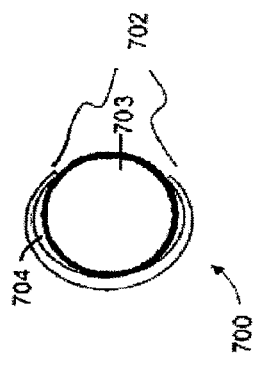
FIG. 6
FIG. 7

METHOD AND APPARATUS FOR DELIVERY OF A LIGATING SUTURE

RELATED APPLICATIONS

This Application claims the benefit under 35 U.S.C. §120 of U.S. application Ser. No. 12/187,486, entitled "METHOD AND APPARATUS FOR DELIVERY OF A LIGATING SUTURE" filed on Aug. 7, 2008, now abandoned, which is herein incorporated by reference in its entirety. application Ser. No. 12/187,486 claims priority under 35 U.S.C. §119(e) to U.S. Provisional Application Ser. No. 60/963,958, entitled "METHOD AND APPARATUS FOR DELIVERY OF A LIGATING SUTURE" filed on Aug. 8, 2007, which is herein incorporated by reference in its entirety.

FIELD OF THE INVENTION

The invention relates to a device or apparatus, systems and methods for medical tissue protrusion removals, and more specifically, to methods for ligating medical tissue protrusions.

BACKGROUND

Nasal polyps are an outgrowth of sinus linings that protrude into the nasal cavities, and are the result of nasal allergy infection and other causes of nasal obstruction, which interrupts the normal function of the sinuses. The nasal blockage caused by polyps further impairs the passage of air through the nasal passages leading to infection, snoring, loss of taste, and disorders of sleep. Furthermore, the nose and sinuses are vital anatomical parts to breathing: they allow incoming air to be warmed, cleaned, and moisturized for transport into the lungs. Therefore, removal of nasal polyps by surgical intervention eliminates obstruction and restores nasal and sinus function. This is critical to respiratory health.

Because removal of polyps, most of which originate in the deep recesses of the nose, demands utilization of a surgical operating team and appropriate anesthesia in a surgical suite, the procedure is costly, inconvenient and associated with the usual post-operative problems such as bleeding, infection, pain, slow recovery and anesthetic side effects.

The present surgical procedure for nasal polyp removal in a blind area is to identify the size and origin of the polyp using an endoscope (light source and lens viewing) and, after stabilizing the tissue to be removed, use a cutting device, ligature and/or cautery to free the protruding lesion from its base, stop bleeding, and extract the polyp from the cavity with a surgical snare. The tissue removal requires several surgical procedures: endoscopy, tissue removal and hemostasis with different instruments prior to extraction of the tissue. Each of these procedures involves time and tissue manipulation utilizing instruments that are single-purpose tools. They cannot be used jointly and, because of the size of the operative field, they need to be used one after another for the planned surgery. In fact, during the tissue removal process, each instrument must be available simultaneously for quick, effective, trouble-free extraction. The presence of post operative bleeding which demands nasal packing is the most troublesome complication for patient and surgeon.

Systems currently in practice almost exclusively remove the nasal polyp by cutting and cauterizing the base which demands use of a surgical suite and anesthesia. No workable substitute system including the use of a non-surgical technique such as ligature application for compression of the polyp base exists.

Since the origin of most nasal polyps is within the sinus cavity, not the nose, the base of the polyp tissue is difficult to identify and encircle. Tying a surgical knot in the small recesses of the nose where most polyps originate is cumbersome and ineffective leading to complications. Instruments that rely on a circular surgical loop for delivery of a ligature at the mouth or ostium of the sinus cannot reach the base of the polyp tissue for removal. For these reasons previously designed instruments for nasal polyp removal by ligature compression of the base of the polyp have not been successful and are not in general use.

Accordingly, there is a need for methods and instruments that address the above mentioned problems and can provide a simple, convenient and rapid approach to this medical procedure. This approach would allow, in most situations, the physician, not necessarily a surgeon, the use of a private medical office rather than a hospital operating suite. It would eliminate the use of an anesthetic and thus eliminate many of the complications of the current procedure providing safety and patient comfort at a fraction of the cost.

SUMMARY

The present invention provides an apparatus for ligating a tissue protrusion, thereby restricting blood flow to the protrusion and thus allowing the tissue to drop off and be eliminated naturally. The device comprises a tubular body having a proximal end and a distal end, a handle positioned at the proximal end, and an endoscope controller operably connected to a cutter blade. The device also has a suture controller that is configured to be operatively coupled with a ligating suture, a curved bridge positioned at the distal end of the instrument with the bridge having a proximal end and a distal end, and an armature, having a proximal end and a distal end, that is configured to releasably retain at least a portion of the ligating suture. The armature is configured to place at least a portion of the ligating suture around the medical protrusion. The suture controller is configured to allow the ligating suture to ligate the medical protrusion while the cutting controller is configured to separate at least a portion of the suture from the ligated medical protrusion.

This invention also provides a new method for ligating a medical protrusion with a suture. The suture is mounted on the apparatus and the device is inserted into the body to reach the site of the medical protrusion. The distal end of the device containing the suture material has a balloon-shaped curved armature of which the larger distal end allows ease of capture of the bulbous shaped polyp and the narrow "V" shaped proximal end of which is configured to guide the constricting suture loop tight to the narrow base of the polyp. In another embodiment, the present invention provides for a ligating device that places an elastized band about the medical protrusion.

Other aspects and advantages of the present invention will become apparent from the following detailed description of the proposed surgical instrument.

DETAILED DESCRIPTION OF DRAWINGS

FIG. 4 is a top view of the distal end of the device 100 of FIG. 1.

FIG. 5 is a bottom view of the distal end of the device 100 of FIG. 1.

FIG. 6 is a side view of the distal end of the device 100 of FIG. 1.

FIG. 7 is a cross section view of the armature according to various aspects of the present invention.

DETAILED DESCRIPTION

As used herein, the term "a" refers to "one or more" unless otherwise mentioned. As used herein, the term "include" refers to "includes without limitation". As used herein, the term "circumscribe" refers to creating a loop around an object or encircling an object. As used herein, the terms "cut" or "cutting" refers to cutting, shearing or disuniting an object.

While various conventional techniques may benefit from the apparatuses and methods discussed herein, another aspect of the present invention is a technique for treating the condition of medical protrusions itself. According to this technique, a ligation is made around the protrusion, and no incision is made. The ligation is intended to be tight such that the blood flow to the protrusion is substantially restricted. Due to the lack of blood supply, the protrusion tissue dies, and eventually the protrusion falls off the patient's body by itself, without requiring any cutting or cauterizing as required by conventional techniques.

Figure 1:
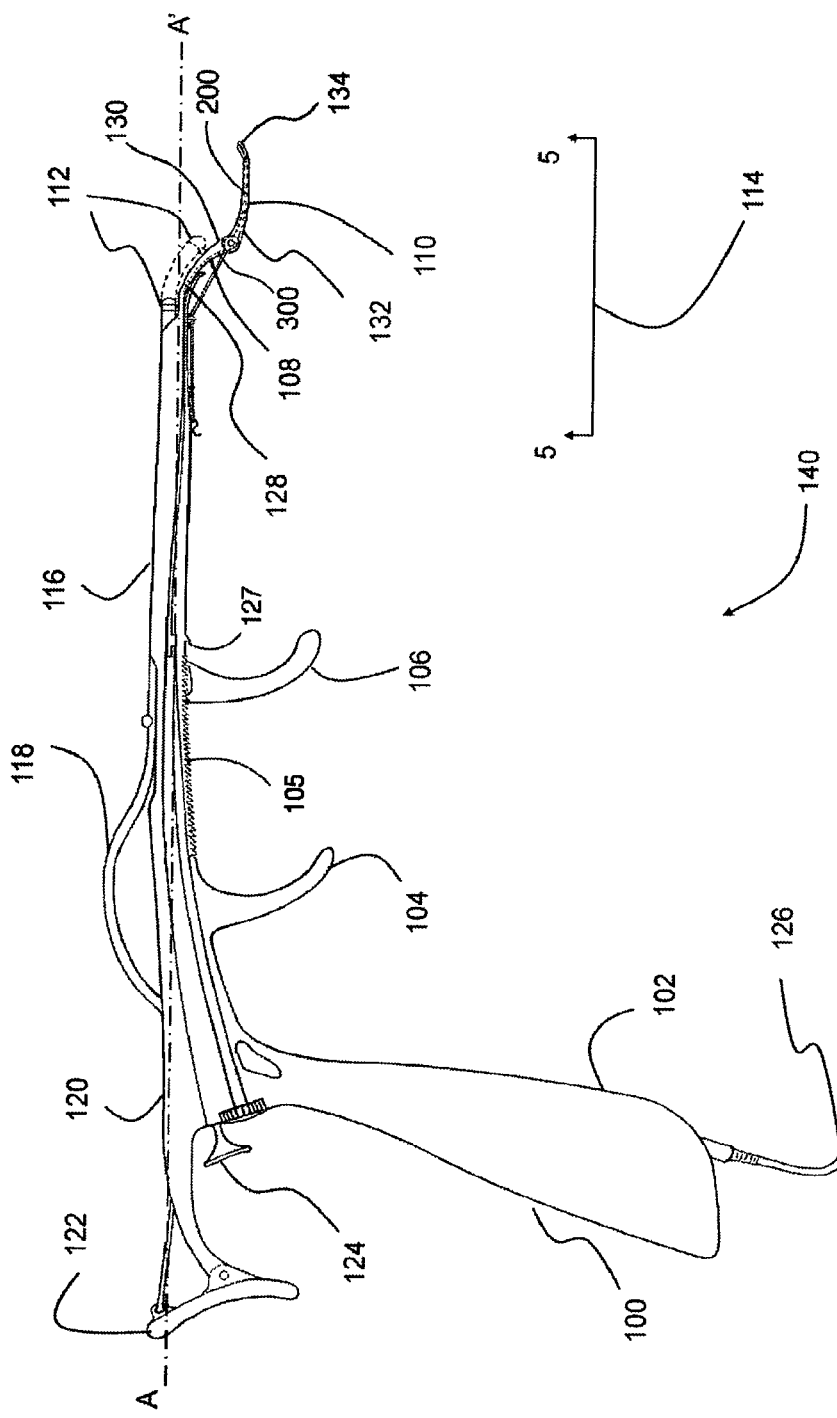
FIG. 1 illustrates an apparatus incorporating a flexible endoscope for ligating a medical protrusion according to an embodiment of the present invention.
Figure 11:
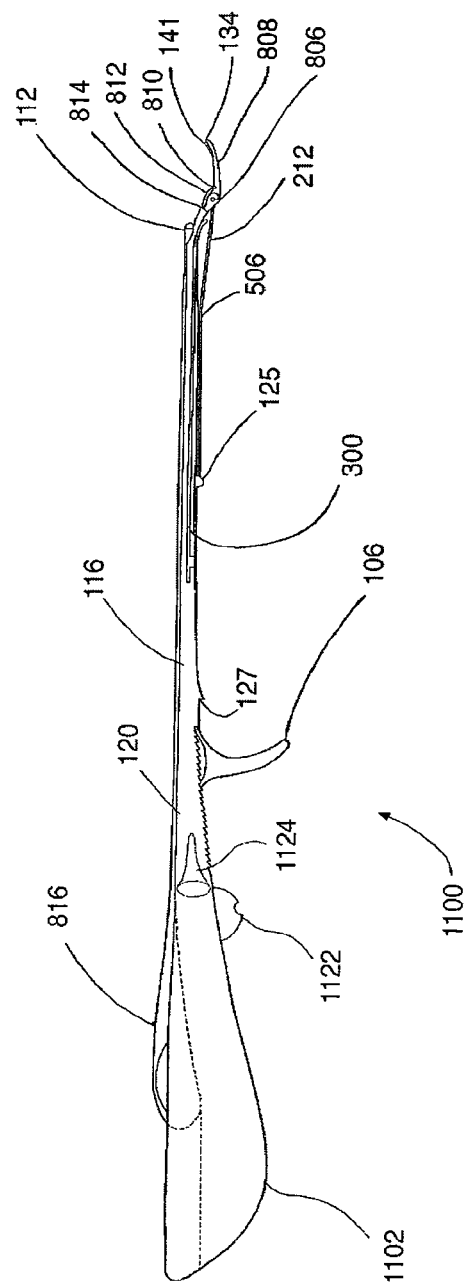
FIG. 11 illustrates an apparatus with a straight handle, and removable and operable armature, for ligation a medical protrusion according to another embodiment of the present invention.

FIG. 1 illustrates an apparatus 140 for ligating a medical protrusion in accordance with certain aspects of the present invention. The apparatus 140 comprises a device 100 for ligating a medical protrusion, an endoscope 112, a ligating suture 200 (FIG. 2), and a cutter blade 300 (FIG. 3). The endoscope 112 has one or more lighting means, such as means that either generate or transport light, for example, fiber optic cables, miniature LEDs, among various others, and one or more image capturing means, such as, digital cameras and analog cameras (still or motion medium), among others. Power and image data transfer for electronics are either contained in the removable section of the handle 100 or are transferred via a power/data cord 126 or via any type of wireless protocol. It is understood that this apparatus could incorporate a replaceable and operable armature as illustrated in 808 (FIG. 8), and a possible handle as illustrated in 1102 (FIG. 11).

Figure 2:
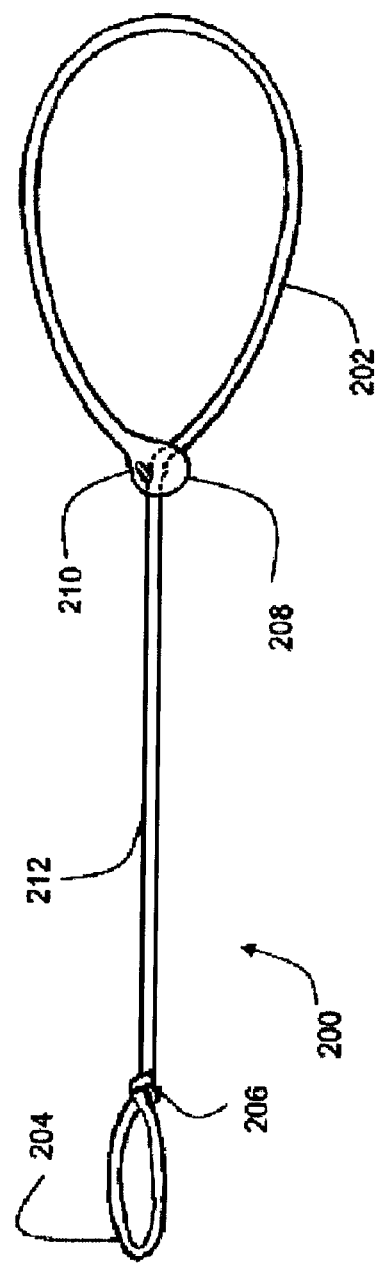
FIG. 2 illustrates a ligating suture according to another aspect of the present invention.
Figure 3:
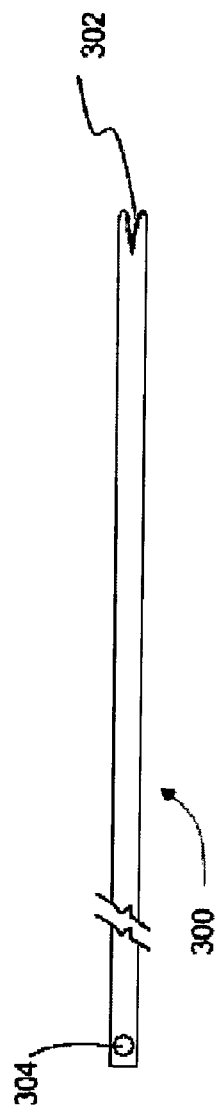
FIG. 3 illustrates a cutter blade according to yet another aspect of the present invention.
Figure 10:
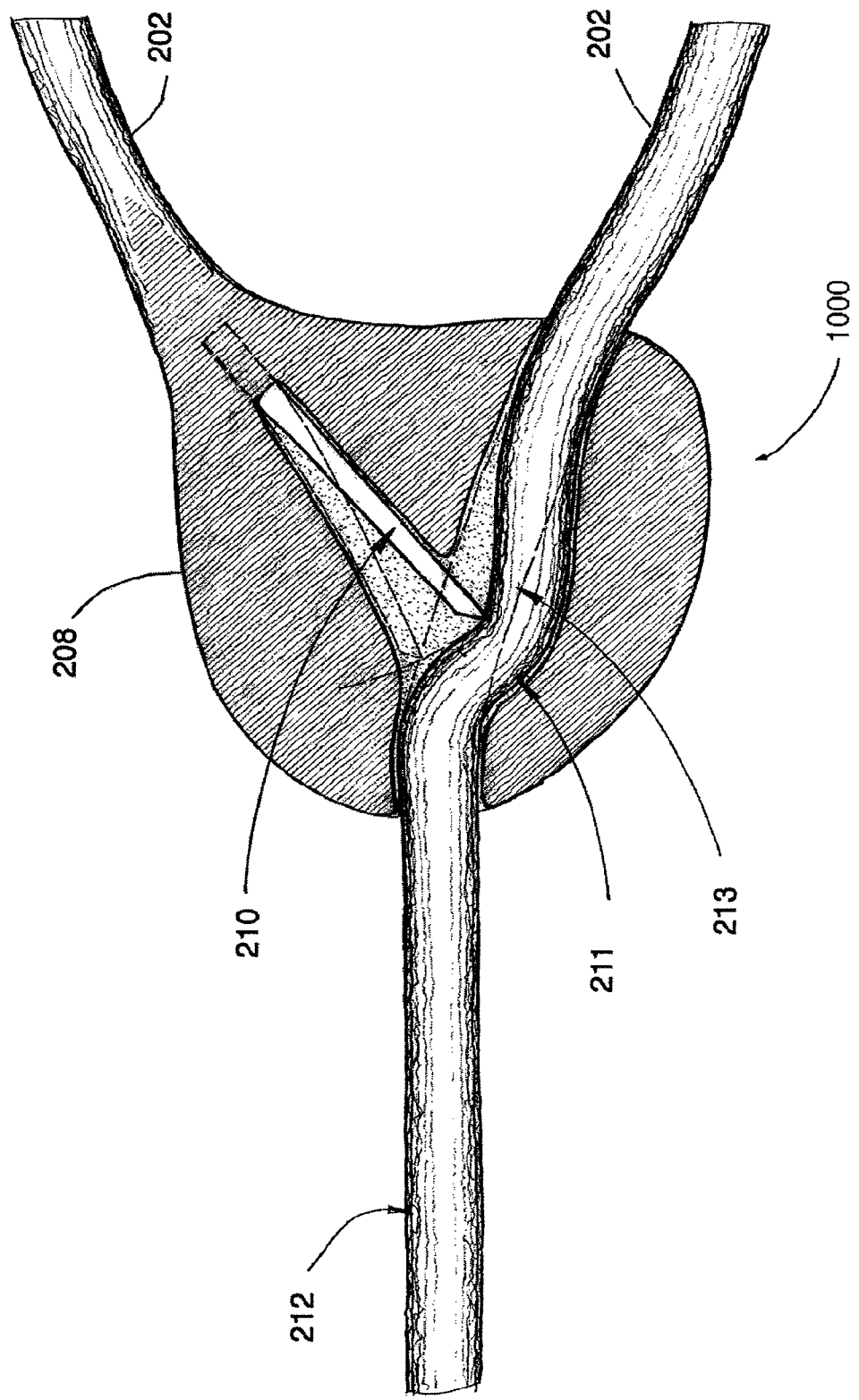
FIG. 10 illustrates further detail of a possible one-way lock which could be incorporated into the ligating loop of the present invention.

FIG. 2 illustrates the suture 200 which is a ligating suture, according to certain aspects of the present invention According to various embodiments, the suture 200 comprises a biodegradable material in a thread-like structure. The suture 200 includes a suture proximal end 204 and a suture distal end 202 connected by an interstitial cord 212. A one-way lock 208 is positioned between the suture distal end 202 and the suture proximal end 204. In certain embodiments the suture distal end 202 has a shape of a loop (shown). Only the suture distal end 202, which is used for ligating the protrusion may be made of a biodegradable material, and the rest of the suture 200 may be made of another material. In the embodiment illustrated by FIG. 2, the suture distal end 202 is a balloon shaped loop. The suture 200 is configured such that pulling the suture proximal end 204 away from the suture distal end 202 constricts the suture distal end 202 loop. According to one embodiment, this constriction is enabled by the one-way lock 208 (a possible one-way lock configuration is illustrated in FIG. 10) which is a preformed ball having a projection 210 embedded at an angle with respect to the suture thread passing through the preformed ball 208. The projection 210 is configured to allow slidable movement of the suture thread in one direction through the one-way lock 208. As illustrated in FIG. 2, this configuration is achieved by having the projection 210 project such that if the cord 212 were to be pulled away from the suture distal loop 202, the projection 210 does not offer any resistance. However, in case of reverse movement, the projection 210 offers resistance to the portion of the engaging suture material. For example, as shown in FIG. 2, the projection 210 prevents movement in the reverse direction by obstructing the sliding motion of the suture material.

According to certain aspects, the projection 210 is made of a biodegradable material, identical to that of the suture 200. However, the material, in one embodiment, in the projection 210 is compressed higher than in the rest of the suture 200, and accordingly the projection 210 has the suture material with a higher density, thereby causing the projection to bite into and restrain the softer suture thread. Those skilled in the art will appreciate that multiple such equivalent configurations can provide a one-way lock in a manner similar to that described of FIG. 2, and all such obvious mechanisms are included within the scope of the present claims.

Further, conventional tied knots need an amount of end length so that they are not untied at an inopportune time, thereby leaving a stub of suture material out of the ligation, which is a cause for potential irritation to the patient and highly undesirable. The one-lock 208 as disclosed herein is not a tied knot. Nor does it require an end length stubbing out. The present suture 200 thus provides for a ligation of a medical protrusion without leaving undesirable knots.

Figure 9:
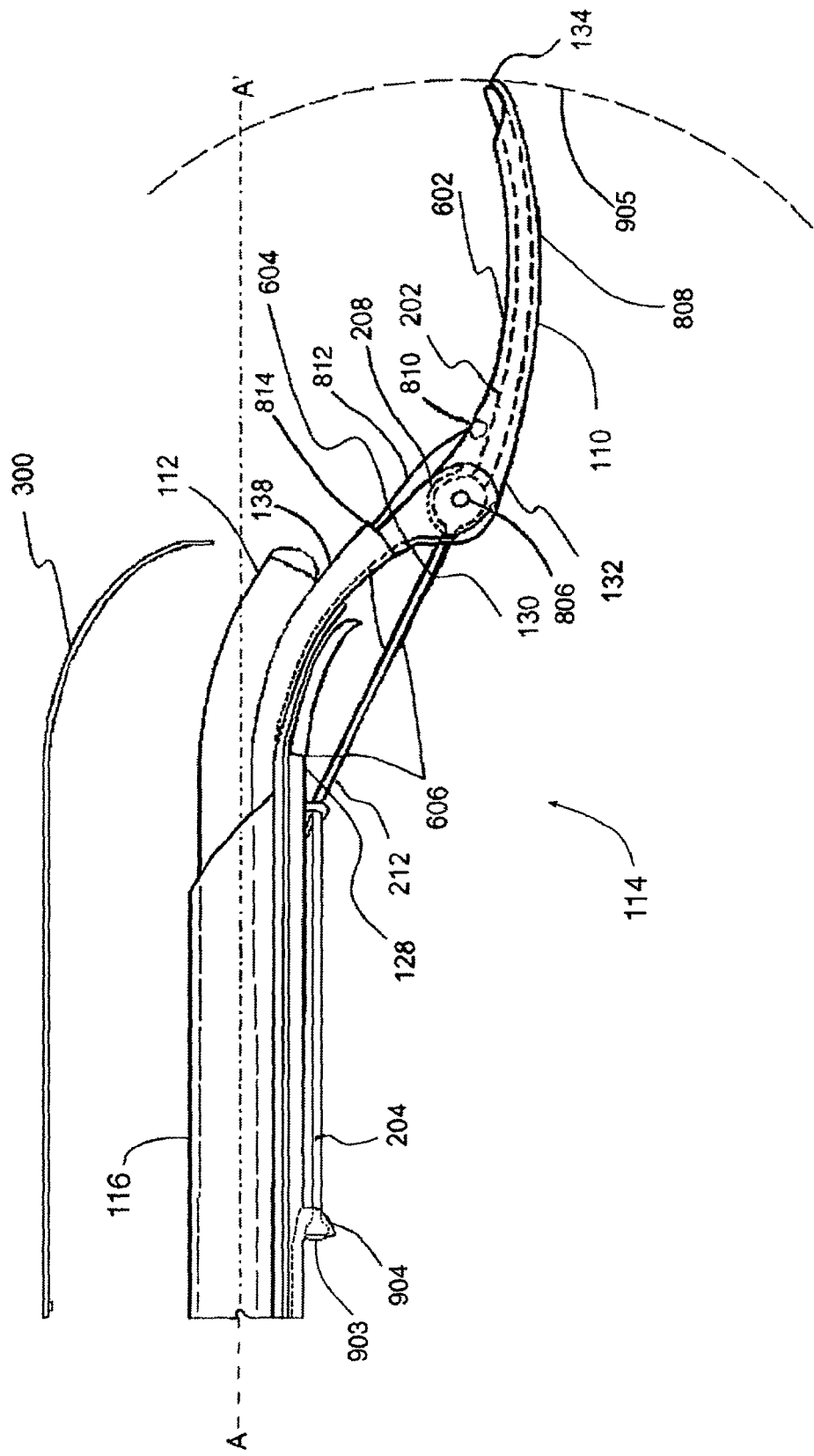
FIG. 9 illustrates further detail of the operable and removable armature shown in the distal end of the apparatus shown in FIG. 8.

The suture proximal end 204 is usable for constricting the suture distal end 202 loop. The pulling action of the suture proximal end 204 enables in constricting the loop 202. As will be apparent to those in the art, the pulling functionality of the suture proximal loop 204 may be implemented in multiple ways. According to one embodiment, the suture proximal end 204 is a preformed ball 903 (FIG. 9) configured to be operably coupled to a cupping means 904 (FIG. 9). The cupping means grips by "cupping" around the suture proximal end 204 preformed ball, and the cupping means are pulled to actuate the pulling of the suture proximal end 204. According to another embodiment, as also illustrated in FIG. 2, the suture proximal end 204 is a loop, configured to be operably coupled to a hooking means (not shown in FIG. 2, but shown in 404 (FIG. 4 and FIG. 6). The hooking means when pulled, pull the suture proximal end 204 thereby constricting the suture distal end 202 loop.

FIG. 3 illustrates the cutter blade 300 according to various aspects of the present invention. According to an aspect, the cutter blade 300 includes a safety blade edge 302 and a cutter blade coupling device 304 to couple to the cutter controller 124. In the embodiment of FIG. 3, the safety blade edge 302 has a "V" shape, which advantageously shears off the cord 212 from the suture distal end 202 more easily than a flat blade, and eliminates the need for an anvil (a base required as support for the flat blade to operate) that may get worn and become less effective with use. Further, the safety blade edge 302 advantageously slices the cord 212 off the suture distal end 202 very near to the one-lock 208, leaving substantially negligible or no thread material extending out from the one-lock 208. This results in a neat cut eliminating potential patient irritation. Further, the cutter blade 300 is a replaceable blade, configured to mate with the apparatus 140 releasably, and may be easily replaced after use. This aspect is particularly advantageous in light of communicable infections, such as for example, HIV, Hepatitis, and other serious transferable diseases among various others. The speed at which things can be handled in dangerous situation is important, and the cutter blade 300 as illustrated above is quickly and easily replaceable with minimal safety concerns because the safety blade edge 302 is concealed to the inside, as illustrated. This advantageously allows for the users to handle the cutter blade without the danger of getting infected unduly, because the sharp edge of the blade is not exposed.

The device 100 for ligating a medical protrusion includes a tubular body 116 having a proximal end 120 and a distal end 108. A handle 102 is positioned at the proximal end 120. It is understood that this apparatus could incorporate a possible straight handle as illustrated in 1102 (FIG. 11) which is in line with the tubular body 116. A finger brace 104 is used to help guide the suture loop over the polyp without accidentally advancing the suture controller. The device further includes an endoscope controller 122 operably connectable to the endoscope 112, a cutting controller 124 operably connected to the cutter blade 300, and a suture controller 106 operatively coupled with the suture 200. A curved bridge 108 is positioned at the distal end 128. The bridge has a bridge proximal end 128 and a bridge distal end 130. The device 100 further includes an armature 110. The armature 110 is positioned in proximity of the bridge 108 and towards the bridge distal end 130. The armature 110 has an armature proximal end 132 and an armature distal end 134. The armature 110 is configured to releaseably retain at least a portion of the suture 200. The armature 110 is configured to place at least a portion of the suture 200 about the medical protrusion. The suture controller 106 is configured to ligate the suture 200 about the medical protrusion, and the cutting controller 124 is configured to operate the cutter blade 300 so as to detach the portion of the suture 200 ligating the medical protrusion from the apparatus 140.

FIG. 4 is a partial top view of the armature 110 loaded with the suture 200. The dotted lines indicate the structure beneath the top covering wall of endoscope 112. The hook 404 is coupled with the suture proximal end 204 (loop) by tilting the suture controller 106 clockwise and moving it forward to the suture load position 127. As will be apparent to those in the art, the coupling functionality of the suture controller 106 as illustrated in FIG. 4 and FIG. 6 may be implemented in multiple ways. The suture controller 106 is configured to pull the suture proximal end 204 (loop) on actuation of the suture controller 106 towards the proximal end of the device 100 whereby the ratchet 105 controls the tension of the suture 200 allowing the user to "feel" the amount of the pressure necessary to keep the cord 212 tight and to facilitate the cutting with the safety blade edge 302. The one-lock 208 is positioned substantially towards the armature proximal end 132. FIG. 5 illustrates a bottom view of the armature 110 along the section 5-5 of FIG. 1. The armature proximal end 132 has a cup 502 (see also 502 of FIG. 6) that holds the one-lock 208 in position and a slot 504 that passes only the suture cord 212. According to certain embodiments, when viewed from the top or bottom, the armature 110 has a balloon shape with the armature distal end 134 having a substantially rounded shape and the armature proximal end 132 having a substantial "V" shape, also referred to as the armature opening 402. In certain embodiments, when viewed from the side (FIG. 6), the armature 110 is curved, such as, for example, convave upwards, convex downwards, among others. In certain embodiments, the curve of the armature 110 is offset towards the armature distal end 134. According to the embodiment illustrated by FIG. 6, the curve is concave upwards and offset 608 towards the armature distal end 134 or the tip 134 of the armature. Further, the armature 110 is positioned at an offset 608 with respect to the tubular body 116 axis A-A'. For example, in the illustrated embodiment, the armature 110 is positioned below the tubular body 116 axis A-A' when viewed from the side. In certain other embodiments, the armature 110 may be positioned above the tubular body 116 axis A-A' when viewed from the side. The armature 110 may be coupled to the device 100 at or around the proximal end 128, such as, for example, to the curved bridge 108 at the bridge distal end 130, in the embodiment illustrated by FIG. 6 and FIG. 9. According to certain aspects, the armature 110 is configured to be releasably coupled to the device 100. That is, armatures of varied shapes or sizes may be mounted on the device 100 in a simple attach and release configuration, as already known in the art, and as also shown in one embodiment in FIG. 8 and FIG. 9.

According to certain embodiments, as also illustrated by FIGS. 4-7, the armature opening 402 is advantageously configured to be parallel to normal tissue around the medical protrusion. Further, the armature distal end 134 is curved upwards (FIG. 6). Also, as illustrated in FIG. 7, the armature 110 has a "C" shaped cross section 700. Edges 702 of the "C" shape provide a narrower opening than the suture 200 thread diameter, while hollow 704 of the "C" section is larger than the suture 200 thread diameter.

According to one embodiment, the armature is configured to receive the removable suture 200 manually. For example, the suture 200 is finger loadable by hooking the one-lock 208 of the suture 200 into cup 502, hooking cord 212 under hook 506, moving hook 404 forward to its load position, hooking loop 204 over hook 404 and finally pressing distal loop 202 into the opening 704 at the inside of the armature with the finger or a thin shaft. Even for armatures having relatively smaller size, this design provides a convenient way to load the suture 200 manually and conveniently, as most human fingers will be able to load the suture conveniently for armatures configured for even small medical protrusions, such as, for example, nasal polyps among others. Further, the suture 200 is easily loadable in its entirety, in a few seconds, and does not require the person loading the suture to be extensively trained. Furthermore, only the suture 200 is required, and no suture cartridges or additional material is needed. In this fashion, the suture 200 can be advantageously loaded quickly in to the same device 100 for subsequent protrusion removal while the patient is still under the influence of relevant medicines, such as, for example, local anesthesia.

Figure 8:
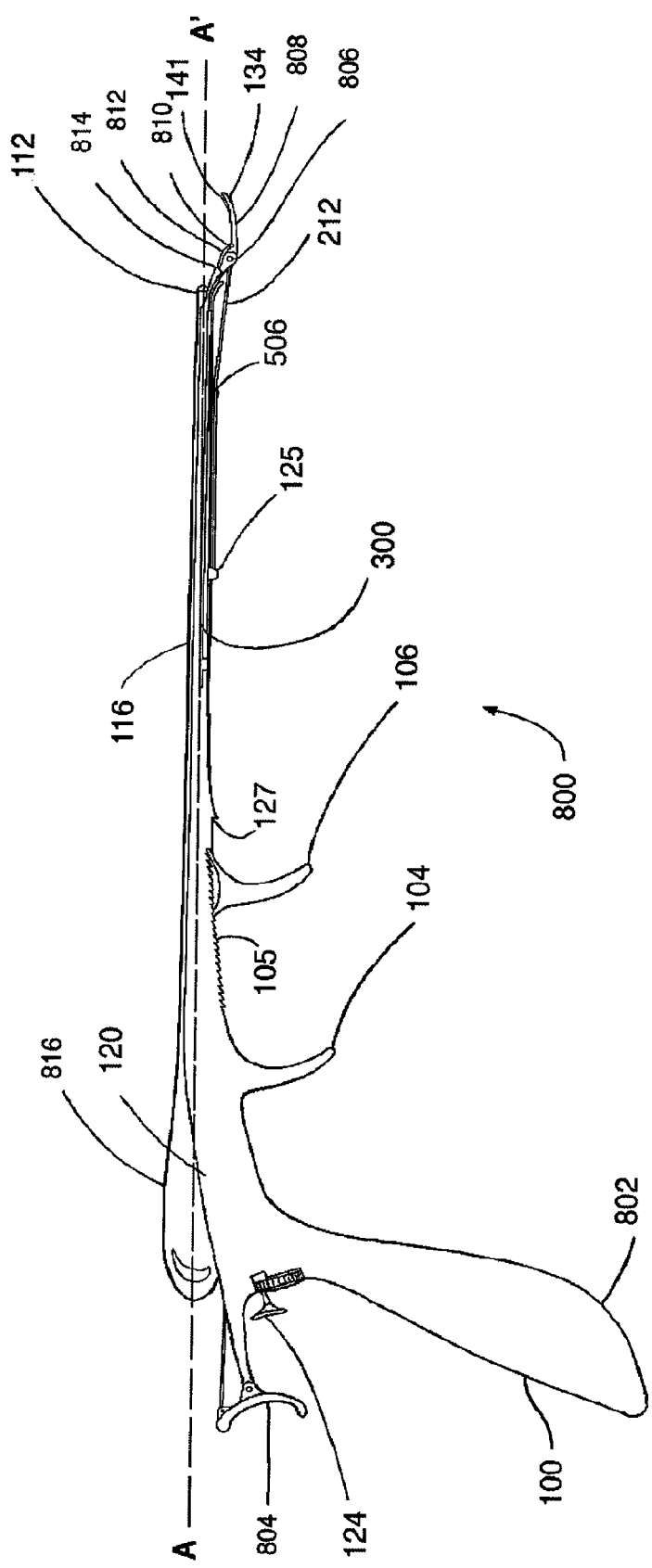
FIG. 8 illustrates an apparatus incorporating an operable and removable armature, and camera for ligating a medical protrusion according to another embodiment of the present invention.

FIG. 8 illustrates another apparatus 800 for ligating a medical protrusion in accordance with certain aspects of the present invention. In this embodiment apparatus 800, with further detail in FIG. 9, illustrates the armature 808 as movable about hinge 806, to allow rotational movement of armature 808 about a rotational axis perpendicular to tubular body 116, along axis A-A', distal end 134 of which follows ark 905 when armature controller 804 is manipulated. The feature in this aspect of this pivot readily allows for the capture of a polyp by allowing for a change in the angle of the opening of the armature in relation to the angle of the polyp. This aspect also has a replaceable head that disassembles at joint 814 to allow alternate heads of different sizes and shapes to be used as needed based on the size and location of polyp and the limitations of the nose and sinus cavity. The controller wire 812 disengages the replaceable heads at the wire pivot lug 810. Further illustrated in this embodiment is a handle 802 which contains apparatus for self contained rechargeable power, and Bluetooth capability or other if desired to project an image to a user adjustable flat screen suspended from a user adjustable boom. It is understood that this embodiment of the apparatus of the present invention could incorporate a flexible endoscope.

FIG. 10 illustrates a possible one-way lock configuration that may be used in the present invention. In an embodiment not shown, the free end of the loop could snap into the body of the one-way lock 208 when necessary to capture a protrusion or entity where there is no access to an open end, such as to act like an instant tourniquet. Further, in an embodiment not shown, this one-way lock configuration with the ability to snap into the body of the one-way lock 208 the proximal end is either grip-able or could be couple to a device.

FIG. 11 illustrates another apparatus 1100 for ligating a medical protrusion in accordance with certain aspects of the present invention. In this embodiment the apparatus 1100 illustrates the handle 1102 in line with the tubular body 116, to allow for greater ease in capturing a polyp located on the head side of the nasal or sinus cavities without the handle interfering with the patient's face. In this aspect, the tilting of the armature is achieved with use of the armature controller wheel 1122. To operate the finger depression is dialed on the armature controller wheel 1122 up towards the distal end of the apparatus or back towards the proximal end. The cutter controller 1124 operates by pressing the finger button on it towards the distal end of the tool. This cutter controller 1224 is spring loaded to return to position and retract the blade. It is understood that this embodiment of the apparatus of the present invention could incorporate the armature 110 as well.

Figure 14:
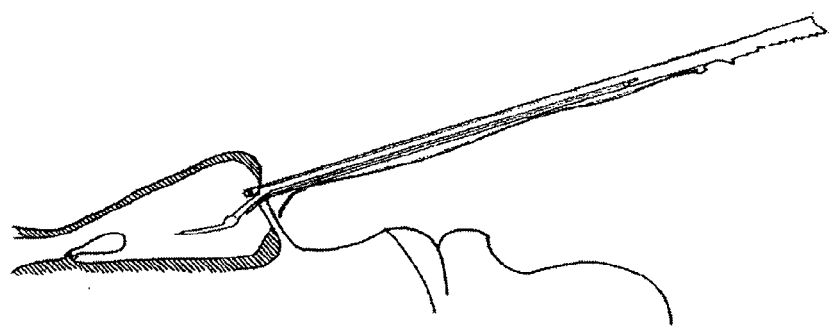
FIGS. 12-14 illustrates each step of a possible procedure for ligating a polyp in the nasal cavity of a patient using the apparatus of the present invention.
Figure 13:
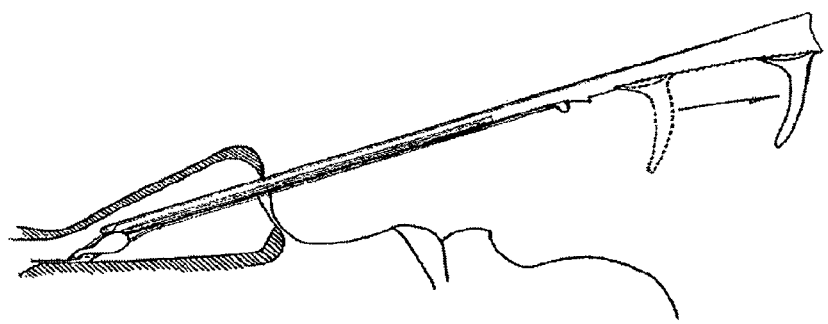
Figure 12:
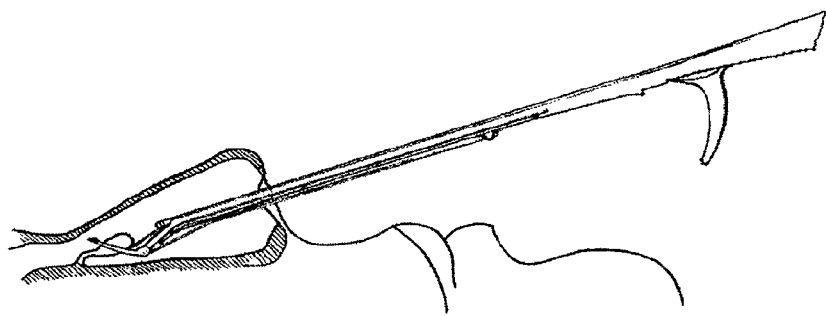

According to another embodiment of the present invention, a method for ligating a medical protrusion using a suture, such as the ligating suture 200 is provided. Ligating the medical protrusion using the ligating suture 200 comprises mounting of the suture 200 to the device 100, negotiating the device 100 to the site of the medical protrusion inside a patient's body, delivering the suture's ligating portion, such as the suture distal end 202 loop over the protrusion to capture at least a portion of the protrusion, constricting the loop 202 about the base of the protrusion, and cutting the loop around the medical protrusion from the rest of the suture 200. FIGS. 12 to 14 illustrate the basic steps involved in ligating a medical protrusion after the mounting of the suture 200 to the device 100 has been performed.

Figure 17:
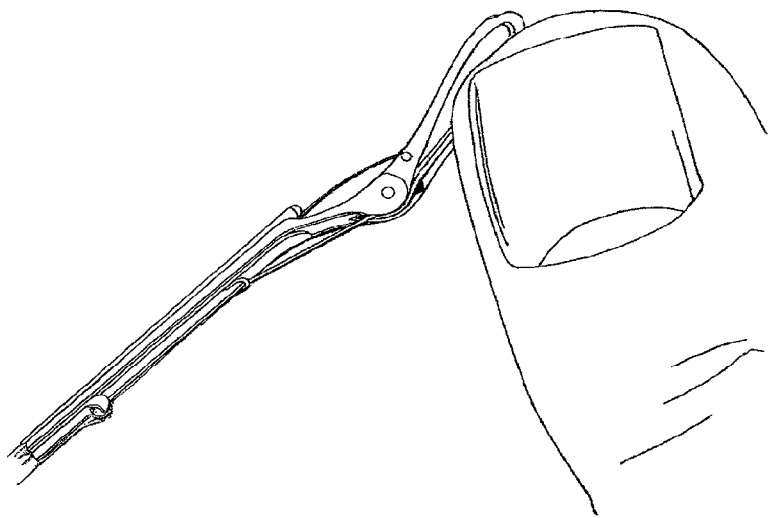
FIGS. 15-17 illustrates the step of a possible procedure for loading the ligating loop into the apparatus of the present invention.
Figure 16:
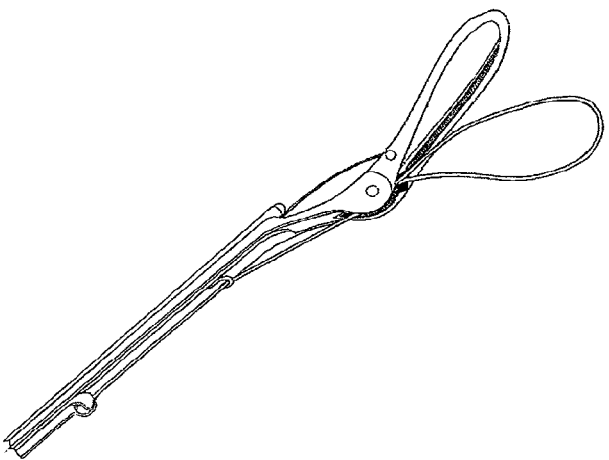
Figure 15:
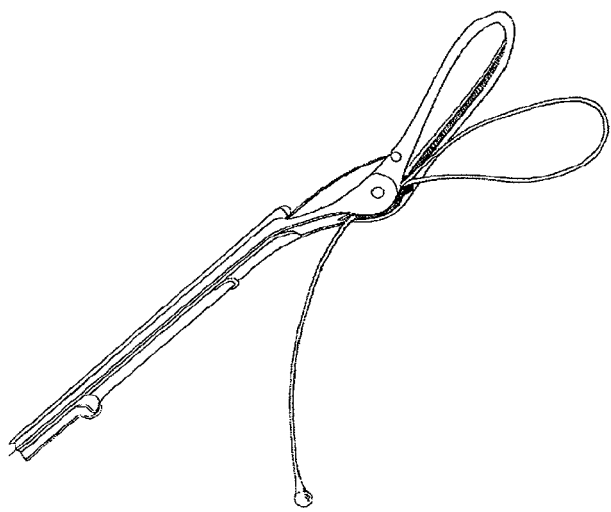

The suture 200 is mounted on a device for ligating a medical protrusion, such as the device 100 in the fashion as described above. Loading the suture is further illustrated in FIGS. 15 to 17. The suture 200 loaded device 100 is then negotiated into a patient's body to the relevant area where the protrusion to be ligated exists. This is effected by inserting the armature 110 or armature 808 of the device 100 into the relevant patient's body part. An endoscope, such as the endoscope 112, provides a view of the path to the remote body part where the protrusion exists, enabling the user of the device 100 to direct the armature 110 or armature 808 to the proximity of the protrusion.

Once the device 100 is in proximity of the desired destination, the device 100 is manipulated by the user over the bulbous of the protrusion deliver the ligating suture 200 to the base of the protrusion. The suture 200 needs to be delivered by the device 100 on the protrusion such that the suture 200 may form a clean, precise and deep ligation around the protrusion. Many features of the device 100, as disclosed herein by various embodiments, are instrumental in providing these features. For example, the suture 200 advantageously comprises of a ligating portion, such as the loop 202 (or "the suture loop"), which has a balloon shape. The armature 110 that holds the loop 202 stiff for ease of delivery to the protrusion site is similarly balloon shaped—the opening of the armature 110 near the armature proximal end 132 is "V" shaped while the armature distal end 134 is approximately semi-circular. Further, the armature 110 is curved when viewed from the side, for example, it is curved concave upwards, and the tip of the armature distal end 134 may be further bent upwards. This bent shape allows the armature distal end 134 to negotiate over difficult to reach protrusions easily. At the same time the "V" shaped armature proximal end 132 opening combined with the concave upward shape allows the opening 132 to get very close to the base of the protrusion, allowing the suture to capture a fuller portion of the protrusion and form a tighter ligation of the protrusion. The armature 110 having a bent tip at the armature distal end 134 advantageously circumscribes the protrusion by peeling out first of the armature distal end 134 and continuing to peel out of the armature 110 successively close to the "V" shaped armature proximal end 132 guiding the loop 202 as close to the base of the polyp as allowed. It is appreciated that this bent tip shape of the armature 110 enables it to circumscribe protrusions having a greater height, or in otherwise difficult to access positions. In certain embodiments where the armature 110 has a balloon shape with the armature distal end 134 having a substantially rounded shape and the armature proximal end 132 having a substantial "V" shape, the armature distal end 134 will allow for capture of a bulbous outer end of the protrusion while the "V" shaped armature proximal end 132 will allow for positioning in close at the thinner base of the protrusion. These features allow for a larger portion of the polyp to be extracted as these features allow for circumscribing protrusions conveniently in comparison with circular type armatured suture loops. In this way, a user may conveniently mount the suture loop 202 on the protrusion, such that the opening of the armature 110 is substantially parallel to the normal tissue lining and generally perpendicular to the protrusion growth. The concave upward shape of the armature 110 allows for the armature to get particularly close to the base of the protrusion circumscribing and therefore capturing a fuller portion of the protrusion.

Constricting the suture loop 202 around the protrusion includes actuating the suture controller 106 to pull the suture proximal end 204. The movement of the proximal end 204 away from the suture loop 202 (suture distal end 202) causes the cord 212 to pull away through the one-way lock 208, reducing the circumference of the suture loop 202 and thereby constricting the suture loop 202 around the protrusion. The user of the device 100 can determine using the endoscope 112, or otherwise, the amount of constriction of the suture loop 202 required to ligate the protrusion.

Cutting the suture loop 202 includes actuating the cutting controller 124 that causes the cutter blade 300 (FIG. 1) to be incident on the suture 200 on the cord 212 very close to the one-lock 208. The incidence of the safety blade edge 302 on the suture 200 causes the cord 212 to cut the suture loop 202. It is intended that the cutter blade 300 is incident on the suture 200 as close to the one-lock 208 as possible, thereby making a clean cut and leaving no or minimal stub. The clean cut made possible by the blade according to various aspects of the present invention eliminates or minimizes potential irritation by such a stub to the patient.

It is believed that the suture with the one-way one-lock discussed above could be replaced with an elastized band. The elastized band would be loaded into the armature in a fashion that would cause the band to be stretched outward in all directions over a convex channel located to the outside of the armature 110. Actuating the elasticized band controller would roll an edge off the armature causing it to snap in place to the bottom side of the armature 110 causing it to contract about the base of the medical protrusion. Suitable elastized bands include those made of rubber and other biological compatible materials.

Figure 18:
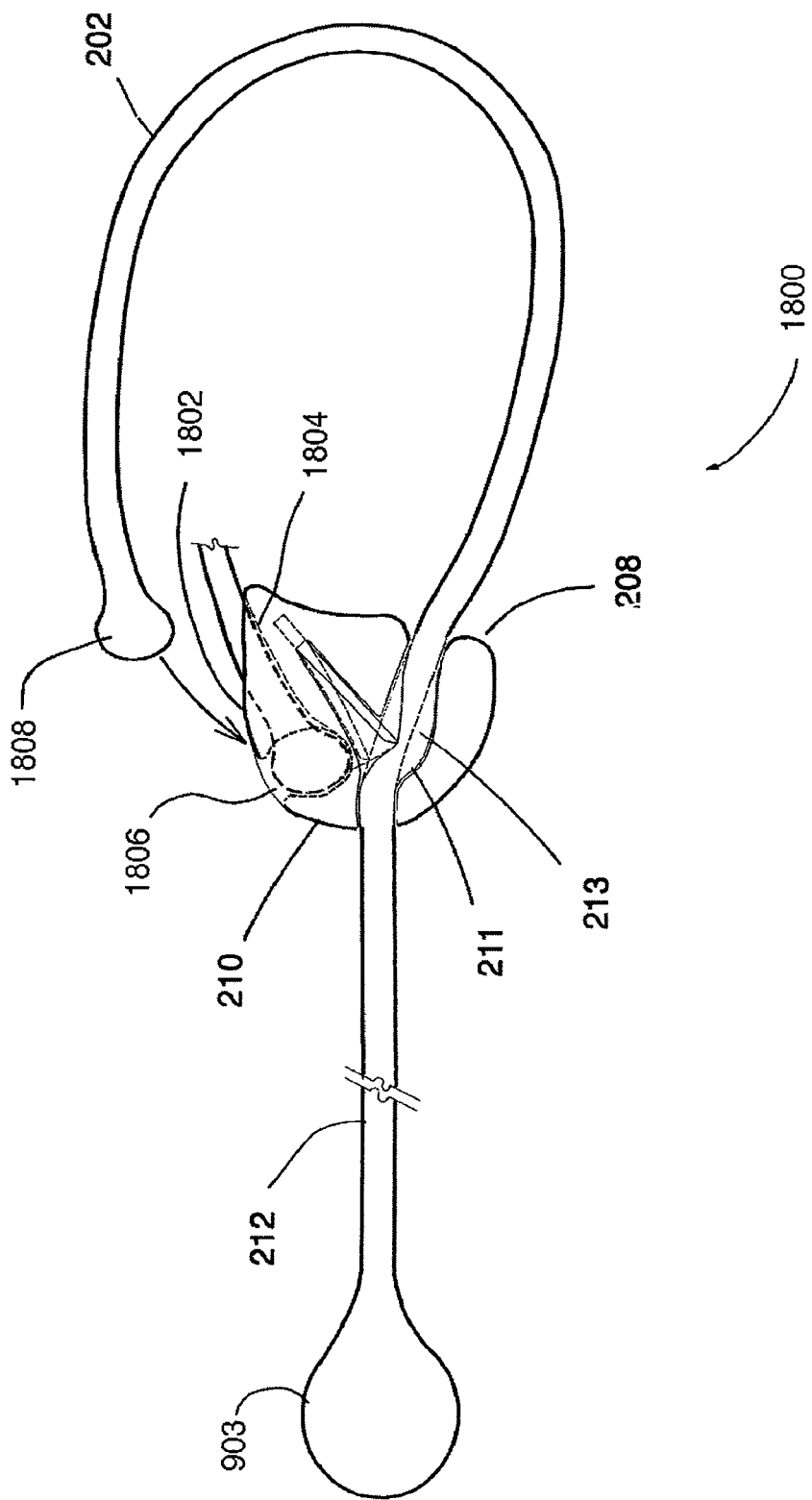
FIG. 18 illustrates another embodiment of the ligating loop of the present invention.

In an alternate configuration the one way device can capture lengths of tissue where the ends of the tissue are not available say in clamping off a vein prior to cutting it or temporarily shutting off a sperm duct for a reversible vasectomy. The device end 1808 shown on FIG. 18 can be looped over a continuous length of tissue and then snapped into a depression 1806 prior to actuating 903. The channel 1802 to 1804 is only wide enough to accept the cord of the suture loop. Removal of the ligation device is as easy as cutting the cord near 1804 with a scalpel. In a further configuration of the above snap-able device the size can be altered to a much larger scale and with an added handle at 903 the device can have EMS and military uses as an instant tourniquet to stop bleeding in emergencies.

The present invention, in its various aspects, provides multiple advantages over conventional apparatuses or methods. For example, the suture as disclosed in accordance with various embodiments advantageously eliminates the tied knot and the associated requirement to have a stub of an extended thread, which is potential source of irritation. The suture further has a balloon shaped armature for holding the suture loop rigid while passing over the ligating protrusion. This balloon shaped suture in conjunction with the device for delivering the suture advantageously helps in capturing a fuller portion of the protrusion, and in capturing protrusions larger in size or in relatively inaccessible configuration. The device as provided in accordance with various aspects, provides for a simpler movement of endoscope, especially for applications, such as, for example, nasal protruding removal. Further, the present invention provides for a cutter blade with enhanced safety features that address the concerns of dangerous infectious conditions such as, for example, HIV, Hepatitis and the like, in the environments that need quick replacements of the cutter blade. Further, the technique of substantially constricting the blood supply to kill the protrusion tissue, eventually causing protrusion removal without requiring any incisions or cauterizing advantageously eliminates the problems associated with managing the wounds, and also provides patient comfort in the long run. Finally, the method to removal nasal polyp with the present invention described herein is minimally invasive, requires no surgery, allows for ambulatory care, and anesthesia is not required though topical anesthesia may used.

While particular embodiments and/or individual features of the present invention and its applications have been illustrated and described, it would be obvious to those skilled in the art that various other changes, modifications and adaptation to other procedures can be made without departing from the spirit and scope of the invention. Further, it should be apparent that all combinations of such embodiments and features are possible and can result in preferred executions of the invention. Therefore, the appended claims are intended to cover all such changes and modifications that are within the scope of the invention.

We claim:

1. A device for ligating a medical protrusion, the device comprising:
   a) a tubular body having a proximal end and a distal end;
   b) a handle positioned at the proximal end of the tubular body;
   c) a suture controller configured to be operatively coupled with a ligating suture;
   d) an armature connected to the distal end of the tubular body and configured to releasably retain at least a portion of the ligating suture, said armature having a balloon shaped loop; and
   e) an armature controller operably connected to the armature through a controller wire, and configured to permit a user to manipulate an angular position of the armature about a rotational axis perpendicular to the tubular body to permit positioning of the balloon shaped loop and placement of at least a portion of the ligating suture about the medical protrusion, wherein the device further comprises a curved bridge positioned at the distal end of the tubular body, said bridge having a proximal end connected with the distal end of the tubular body and a distal end connected to the proximal end of the armature.

2. The device of claim 1, wherein the armature is readily removable.

3. The device of claim 1, wherein the armature is connected to the tubular body through a hinge, and configured such that the armature is rotatable about the hinge.

4. The device of claim 1, further comprising an endoscope controller operably connectable to an endoscope.

5. The device of claim 4, wherein the endoscope has at least one lighting means and at least one image capturing means positioned at the distal end, wherein the endoscope is configured to be movable with respect to the device allowing the user to visually capture the medical protrusion to be ligated.

6. The device of claim 1, wherein manipulation of the suture controller is configured to cause the ligating suture to ligate the medical protrusion.

7. The device of claim 1, further comprising a cutting controller operably connectable to a cutter blade.

8. The device of claim 7, wherein the cutter blade is removable.

9. The device of claim 7, wherein the device is configured such that the cutter blade cuts the suture.

10. The device of claim 9, wherein the device is configured such that the cutter blade cuts the suture in such a way as to leave little excess suture material with the ligated medical protrusion.

11. The device of claim 1, wherein the balloon shaped loop has a distal end that is round and a proximal end that is "V" shaped.

12. The device of claim 1, wherein the armature is offset with respect to the tubular body axis.

13. The device of claim 1, wherein the armature is configured to receive the removable ligating suture manually.

14. The device of claim 1, wherein the armature has "C" shaped cross section.

15. The device of claim 14, wherein the edges of the "C" shaped armature cross section are configured to provide a narrower opening than the suture diameter.

16. The device of claim 1 further comprising a ligating suture releasably retained in the armature, the ligating suture comprising a ligating loop having a distal one way locking loop and a proximal support member.

17. The device of claim 16, wherein the ligating suture is configured such that pulling the support member in the proximal direction, causes the constriction of the distal one-way locking loop when circumscribed about a medical protrusion.

18. The device of claim 16, wherein the one-way locking device comprises a preformed ball with a central channel through which the suture passes.

19. The device of claim 16, wherein the ligating suture is biodegradable.

\* \* \* \* \*